United States Patent
Edwards et al.

(10) Patent No.: US 6,405,138 B1
(45) Date of Patent: Jun. 11, 2002

(54) DETERMINATION OF SILVER IN A PHOTOGRAPHIC SOLUTION

(75) Inventors: Stephen J. Edwards, Pinner; Joanna L. Evans, Rayners Lane; John J. Mcbride, Bushey, all of (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/213,165

(22) Filed: Dec. 17, 1998

(30) Foreign Application Priority Data

Dec. 17, 1997 (GB) .............................................. 9726534

(51) Int. Cl.⁷ .......................... G01N 31/00; G06F 19/00
(52) U.S. Cl. .......................................... 702/23; 702/25
(58) Field of Search ....................... 702/22–27, 29–32, 702/100, 183; 700/266; 205/775, 786.5, 789, 789.5; 204/100, 406, 407, 409, 416; 422/76

(56) References Cited

U.S. PATENT DOCUMENTS

| | | | | |
|---|---|---|---|---|
| 2,886,771 A | 5/1959 | Vincent | ...................... | 324/438 |
| 3,278,399 A | * 10/1966 | Budd | ....................... | 205/789.5 |
| 3,616,412 A | * 10/1971 | Gnage | .......................... | 204/402 |
| 4,218,746 A | * 8/1980 | Koshiishi | ..................... | 205/789 |
| 4,530,748 A | * 7/1985 | Zuwala et al. | ............... | 204/273 |
| 4,978,433 A | * 12/1990 | Iwano et al. | ................. | 205/494 |
| 5,162,106 A | * 11/1992 | Kunda et al. | ............... | 423/511 |
| 5,456,811 A | * 10/1995 | Edwards et al. | ............ | 205/780 |
| 5,500,125 A | * 3/1996 | Horn et al. | .................. | 210/668 |
| 5,951,844 A | * 9/1999 | Jansen et al. | ................ | 205/571 |

FOREIGN PATENT DOCUMENTS

GB 958422 5/1964

* cited by examiner

*Primary Examiner*—Marc S. Hoff
*Assistant Examiner*—Manuel L. Barbee
(74) *Attorney, Agent, or Firm*—Chris P. Konkol

(57) ABSTRACT

A method and apparatus are provided in which silver ions are removed from a photographic fixer solution in a simple and efficient manner. The electrical conductivity of the solution is measured, which is effectively that of the fixer (thiosulphate). The electrical potential of the solution is measured between two electrodes immersed therein. A predetermined algorithm is applied to the two values to determine the silver ion concentration. If this is above a predetermined level, a silver recovery unit is activated. The measurements allow this unit to operate more efficiently than hithertobefore.

13 Claims, 2 Drawing Sheets

DETERMINATION OF SILVER IN A PHOTOGRAPHIC SOLUTION

FIELD OF THE INVENTION

This invention relates to the determination of the quantity of a first component in a solution that contains a second component of appreciably higher electrical conductivity, and is particularly, though not exclusively, relevant to the determination of the quantity of silver in a photographic fixing solution.

BACKGROUND OF THE INVENTION

Although the invention is more generally applicable, for convenience of explanation only, it will be described with reference to photographic processing.

The processing of photosensitive material, film or paper, entails the material being passed sequentially through baths containing developing, bleach and fixing solutions. Silver halides are produced in the developing step, and the fixing step converts these into silver ion complexes that are soluble in water, and which may be removed in a subsequent washing step. Thiosulphates, of sodium or ammonium, are the commonly-used fixing agents. As the concentration of the dissolved halides increases, the time needed to fix the image in the material increases. In order to obtain uniform processing conditions, in a mini-lab for example, it is desirable to maintain the fixing time substantially constant. To this end, the fixer is replenished with fresh solution from time-to-time, usually in dependence on the area of material that has been processed. The effluent from the processing thus contains a quantity of silver ions. Environmental and cost considerations require that these components are not simply fed as waste to a drain. It is known to supply such effluent to apparatus for removing the silver from the solution, which is then recovered for further use.

Problem to be Solved by the Invention

A silver recovery unit operates efficiently only when the concentration of silver in the solution is above a defined minimum value. Thus, it is known to measure the quantity of silver in solution, for example in the fixer bath, and to operate the unit only under efficient conditions. Accurate determination of the quantity of silver ions in a fixer solution has hitherto been difficult precisely due to the presence of the thiosulphate, which is itself electrically conductive.

It will be appreciated that a similar problem can arise in other applications.

SUMMARY OF THE INVENTION

In accordance with one aspect of the present invention, there is provided a method of determining the quantity of a first component in a solution that contains a second component of appreciably higher electrical conductivity, the method comprising the steps of:

(a) measuring the electrical conductivity of the solution;

(b) measuring the electrical potential between two electrodes immersed in the solution; and (c) applying a predetermined algorithm to the measured values of conductivity and potential, thereby to determine the said quantity.

Electrical conductivity is considered to be "appreciably higher" if measurement of the conductivity of the solution as a whole can be taken as being substantially the conductivity of the second component alone.

Preferably, the measurements of steps (a) and (b) are made sequentially, thereby eliminating any interference between the two measurements.

The said quantity of the first component may comprise the concentration of silver ions, and the solution may comprise a photographic fixing agent, preferably a thiosulphate, of sodium or ammonium for example. Particularly, though not exclusively, in this case, one of the electrodes may be a silver electrode and the other electrode may be a reference electrode. A suitable silver electrode, as commonly used in pH measurements, is disclosed, for example, in the book "pH Measurement—Fundamentals, Methods, Applications, Instrumentation" by Helmuth Galster (VCH 1991).

The method of the invention may comprise the steps of supplying a signal in accordance with the said quantity to apparatus for recovering said first component from the solution, and operating the recovery apparatus only when that quantity has a predetermined value, preferably when said quantity is above a predetermined minimum value.

The particular algorithm to be applied to the measured values is to be determined empirically, in dependence on the concentration of the thiosulphate and of the silver ions. An example for a typical arrangement for measuring the quantity of silver is:

$$V_{Ag} = a\ln(Ag^+) + \left(\frac{C_d}{b} - c\right)$$

where, $V_{Ag}$ is the electrical potential measured between the two electrodes in the solution, $Ag^+$ is the concentration of silver ions, $C_d$ is the conductivity of the solution, and a, b and c are known constants.

The steps of the method may be carried out continuously, or alternatively only from time-to-time as required.

In accordance with a further aspect of the present invention, there is provided apparatus for determining the quantity of a first component in a solution that contains a second component of appreciably higher electrical conductivity, comprising:

(a) a vessel for containing the solution;

(b) means for measuring the electrical conductivity of the solution;

(c) two electrodes arranged to be immersed in spaced-apart relationship in the solution in the vessel;

(d) means for measuring the electrical potential between the two electrodes; and (e) means for receiving signals in accordance with the measured values of conductivity and potential, said receiving means being arranged to determine the said quantity of the first component in the solution.

Preferably, and particularly for the recovery of silver from a solution, one of said electrodes is a silver electrode and the other electrode is a reference electrode.

Advantageously, the apparatus comprises apparatus for recovering the first component from the solution, said recovery apparatus being arranged to receive the solution from the vessel, the recovery apparatus being arranged to be operated only on receipt of a signal from the receiving means indicating that the quantity of said first component has a predetermined value, preferably when said quantity is above a predetermined minimum value.

Advantageous Effect of the Invention

Hitherto, the quantity of silver in the fixer solution has been determined from the potential measurement alone. In accordance with the present invention, a correction is made to this measurement to take into account the conductivity of the thiosulphate. The resulting more accurate measurement of the amount of silver in the solution allows a finer control of the subsequent silver recovery unit, that is to say, allows the unit to be operated for a longer time on a given solution. This improved efficiency results not only in the cost saving of recovering more silver, but also in a correspondingly cleaner effluent from the unit, which may be disposed of more conveniently. It has been found that using the present invention, the concentration of silver ions in a fixer solution can be determined to within ±10%.

BRIEF DESCRIPTION OF THE DRAWINGS

A method of, and apparatus for, determining the quantity of a first component in a solution that contains a second component of appreciably higher electrical conductivity, will now be described, by way of example, with reference to the accompanying drawings, in which.

DETAILED DESCRIPTION OF THE INVENTION

Figure 1:
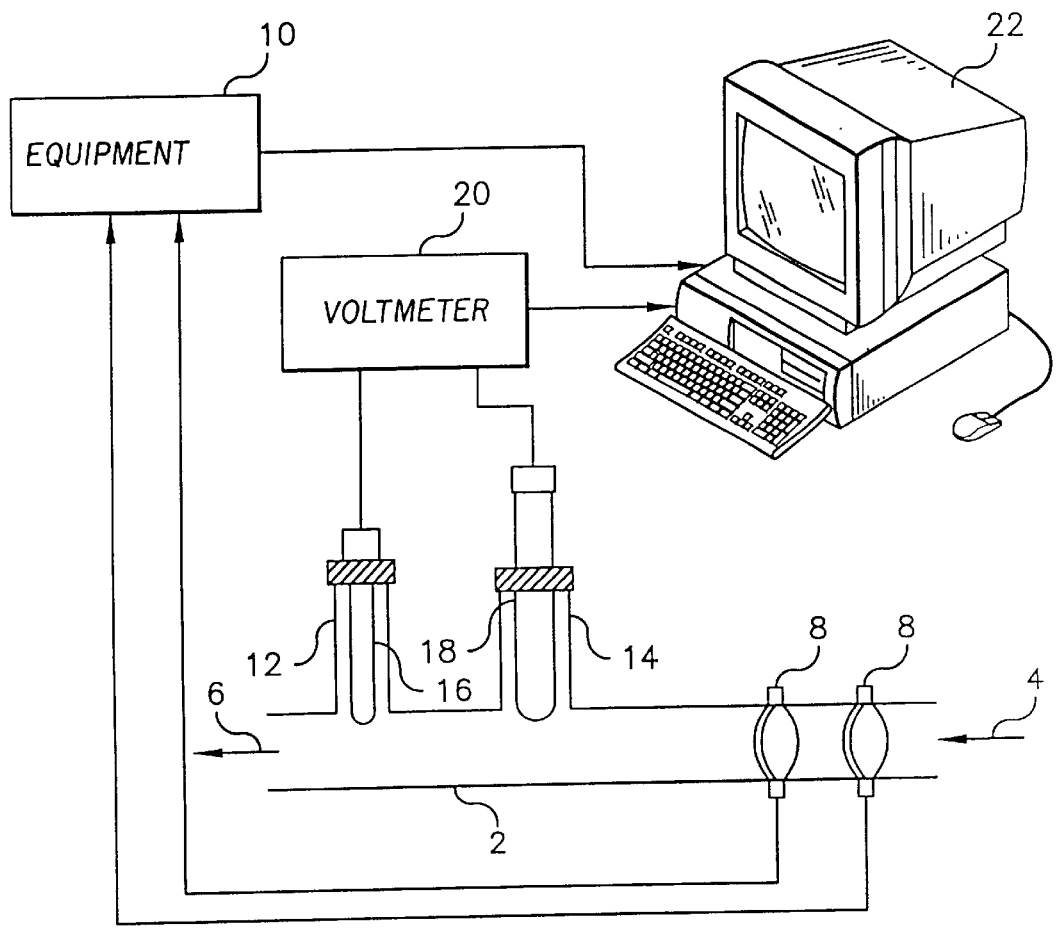
FIG. 1 is a schematic diagram of a laboratory apparatus for the measurement of the concentration of silver ions in a photographic fixer solution.

Referring to FIG. 1, a photographic fixer solution containing sodium thiosulphate and silver ions is passed into a cylindrical laboratory sampling vessel 2 at one end 4 and removed from its other end 6. A spaced-apart pair of induction coils 8 is disposed around the vessel 2. Each coil 8 is connected to equipment 10 that measures and displays the electrical conductivity of the solution passing through the vessel 2. The vessel 2 has two arms 12 and 14 extending to one side thereof beyond the coils 8. The sidearm 12 has a silver electrode 16 sealed thereinto such that its tip projects slightly into the main cylindrical portion of the vessel 2, and the sidearm 14 has a reference electrode 18 similarly arranged. The electrodes 16, 18 are connected to a meter 20 that displays the electrical potential therebetween. The output from the conductivity-measuring equipment 10 and the voltmeter 20 is supplied to a computer 22.

An empirically-derived algorithm is stored in the computer 22 that relates the inputted values of conductivity and potential to the concentration of silver ions in the solution passing through the vessel 2, and displays the result. The following algorithm has been used for a particular configuration of the equipment:

$$Ag(\text{ppm}) = \text{anti}\left[\frac{\left\{\text{Potential}-\left(\frac{\text{Conductivity}}{1.73}\right)\right\}+420.17}{60.83}\right]$$

Figure 2:
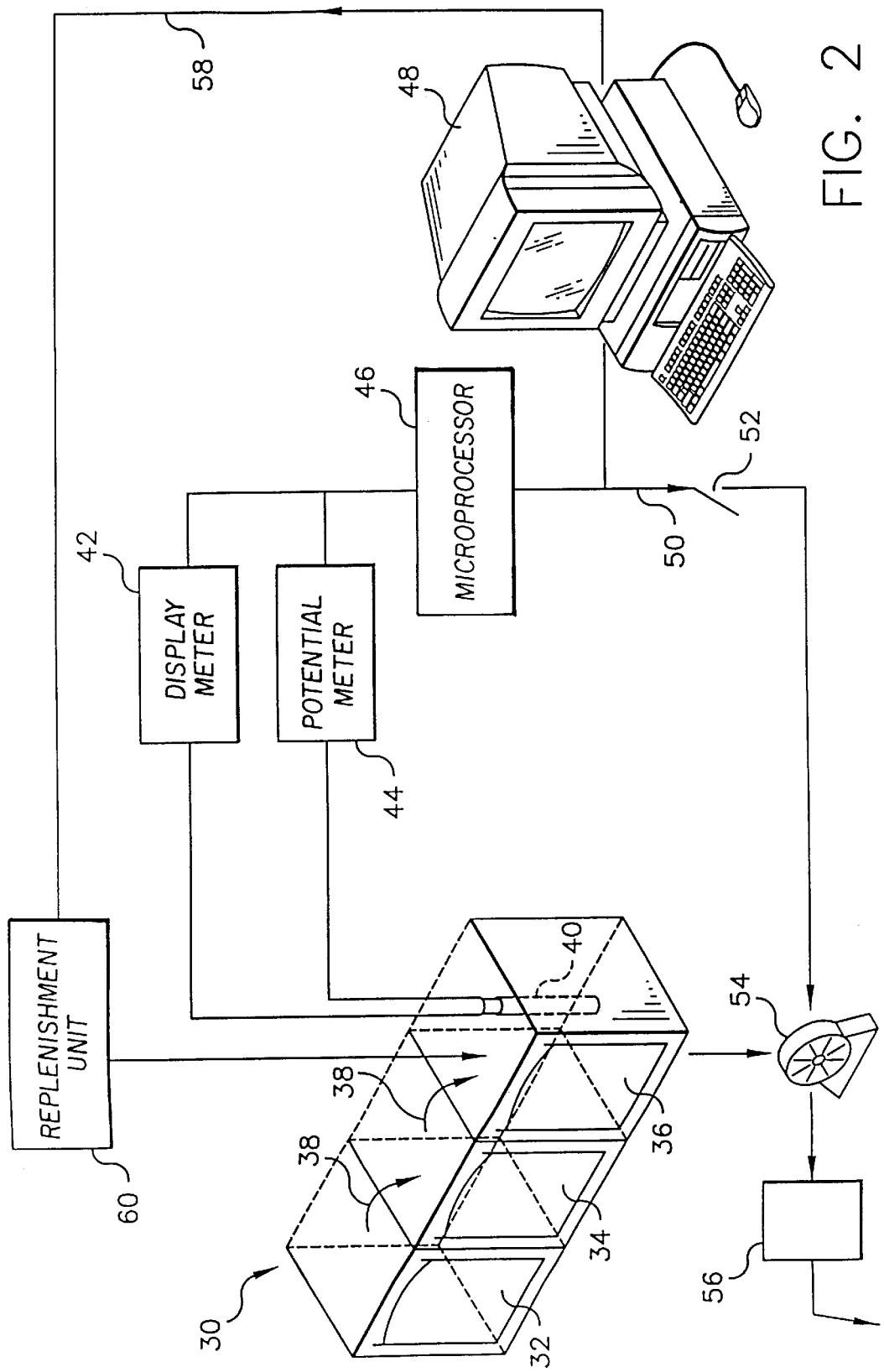
FIG. 2 is a schematic diagram of a photoprocessor incorporating the invention together with a silver recovery unit.

Referring to FIG. 2, a commercial photoprocessor comprises a tank 32 of developing solution, a tank 34 of bleach solution, and a tank 36 of fixer solution. The photosensitive material is shown schematically at 38 transferring firstly from the developer tank 32 into the bleach tank 34 and then into the fixing tank 36. A probe shown schematically at 40 is immersed in the solution in the fixing tank 36. The probe 40 corresponds functionally to the conductivity coils 8 and the silver and reference electrodes 16 and 18 of FIG. 1. One output from the probe 40 is fed to a conductivity measuring station and display meter 42 and another output is fed to a potential meter 44. Output from the meters 42 and 44 is supplied to a microprocessor 46, which may be a stand-alone unit or which may form part of a computer 48.

A control signal line 50 extends from the microprocessor 46 via a switch 52 to a pump 54 that is arranged to pump solution from the fixing tank 36 to a silver recovery unit 56, as shown by the arrows A and B. A control signal line 58 extends from the computer 48 to a replenishment unit 60 for supplying replenisher solution to the fixing tank 36, as shown by the arrow C.

In operation, either continuously or from time-to-time, the output from the probe 40 is assessed by the microprocessor 46 and computer 48. If the computed silver ion concentration level exceeds a predetermined value the microprocessor 46 closes the switch 52 as to operate the pump 54. Fixer solution is removed from the tank 36 and fed to the silver recovery unit 56. Recovered silver is removed, and the remainder of the solution is disposed in an approved manner. Whenever the measured silver ion concentration is below the predetermined value, operation of the recovery unit 56 would not be economical and the microprocessor 46 ensures the switch 52 is open under these conditions.

Also from time-to-time, in response to the data analysed in the computer 48, a signal is fed along the line 58 to activate the replenishment unit 60 for supplying fresh fixer solution into the tank 36. The replenishment unit 60 is operated, when the silver recovery unit 56 is not being operated, in response, for example, to a pre-determined volume of photographic material having been processed.

The invention thus provides a particularly simple and efficient method of, and apparatus for, recovering silver from a photographic fixer solution. It will be appreciated that other components in solution may be separated in accordance with the present invention.

What is claimed is:

1. A method of determining the quantity of a first component in a solution that contains a second component of appreciably higher electrical conductivity, the method comprising the steps of:
    (a) measuring the electrical conductivity of the solution;
    (b) measuring the electrical potential between two electrodes immersed in the solution; and
    (c) applying a predetermined algorithm to the measured values of conductivity and potential, the algorithm mathematically relating the measured values of conductivity and potential in combination in the same equation, to the quantity of the first component in the solution, thereby to determine the said quantity.

2. A method according to claim 1, wherein the measurements of steps (a) and (b) are made sequentially.

3. A method according to claim 1, wherein the said quantity of the first component comprises the concentration of silver ions, and wherein the solution comprises a photographic fixing agent.

4. A method according claim 3, wherein the photographic fixing agent is a thiosulphate.

5. A method according to claim 1, wherein one of the electrodes is a silver electrode and the other electrode is a reference electrode.

6. A method according to claim 1, comprising the steps of supplying a signal in accordance with the said quantity to apparatus for recovering said first component from the solution, and operating the recovery apparatus only when the quantity has predetermined value.

7. A method according to claim 6, wherein the apparatus is operated when the predetermined value is above a predetermined minimum value.

8. A method according to claim 1, wherein the first component is silver and the predetermined algorithm is defined as follows:

$$Ag^+ = e^{x/a}$$

in which,

Ag$^+$ is the concentration of silver ions in the solution; and $$x = \text{potential} - \frac{\text{conductivity}}{b} + c;$$

wherein potential is the electrical potential measured between the two electrodes immersed in solution;

conductivity is the conductivity of the solution; and a, b and c are constants.

9. A method according to claim 8, in which the constants are about a=60.83, b=1.73, and c=420.17.

10. Apparatus for determining the quantity of a first component in a solution that contains a second component of appreciably higher electrical conductivity, comprising:

(a) a vessel for containing the solution;

(b) means for measuring the electrical conductivity of the solution;

(c) two electrodes arranged to be immersed in spaced apart relationship in the solution in the vessel;

(d) means for measuring the electrical potential between the two electrodes; and, (e) means for receiving signals in accordance with measured values of conductivity and potential, said receiving means being arranged to determine the said quantity of the first component in the solution, in accordance with a predetermined algorithm that mathematically relates the measured values of conductivity and potential in combination in the same equation, to the quantity of the first component in the solution.

11. Apparatus according to claim 10, wherein one of said electrodes is a silver electrode and the other electrode is a reference electrode.

12. Apparatus according to claim 10, comprising apparatus for recovering the first component from the solution, said recovery apparatus being arranged to receive the solution from the vessel, and wherein the recovery apparatus is arranged to be operated only on receipt of a signal from the receiving means indicating that quantity of said first component has a predetermined value.

13. An apparatus according to claim 12, wherein the apparatus is arranged to be operated when the quantity of the first component is, above a predetermined minimum value.

* * * * *